United States Patent [19]

Kulla et al.

[11] Patent Number: 4,708,936
[45] Date of Patent: Nov. 24, 1987

[54] PROCESS FOR THE CONTINUOUS PRODUCTION OF L-CARNITINE

[75] Inventors: Hans Kulla, Visp; Pavel Lehky, Naters; Armand Squaratti, Brig, all of Switzerland

[73] Assignee: Lonza Ltd., Gampel, Switzerland

[21] Appl. No.: 717,546

[22] Filed: Mar. 29, 1985

[30] Foreign Application Priority Data

Feb. 27, 1985 [CH] Switzerland ............................ 890/85

[51] Int. Cl.$^4$ ........................ C12P 13/00; C12P 13/01
[52] U.S. Cl. .................................... 435/128; 435/106; 435/287; 435/824; 435/825
[58] Field of Search ............... 435/128, 106, 287, 824, 435/825

[56] References Cited

U.S. PATENT DOCUMENTS

4,371,618 2/1983 Cavazza ............................. 435/128

FOREIGN PATENT DOCUMENTS

0122794 10/1984 European Pat. Off. .

OTHER PUBLICATIONS

Ornston et al., *Biochemical and Biophysical Research Communications*, vol. 36, No. 1, (1969), pp. 179–184.

*Perry's Chemical Engineers Handbook*, 6th Edition, (1984), pp. 27–7.

J. H. Miller, "Experiments in Molecular Genetics", Cold Spring Laboratory, (1972), pp. 121 to 143, Experiments 13 through 17.

P. Gerhardt et al., (eds.), Manual of Methods for General Bacteriology, Am. Soc. for Microbiology, (1981), pp. 222 to 242.

Kulla et al., Arch. Microbiol. 135, 1 (1983), pp. 1 to 7.

J. P. Vandecasteele, Appl. Environ, Microbiol. 39, pp. 327 to 334, (1980).

Lindstedt et al., Biochemistry 6, pp. 1262–1270 (1967).

Lindstedt et al., Biochemistry 16, pp. 2181–2188 (1977).

*Primary Examiner*—Charles F. Warren
*Assistant Examiner*—Elizabeth A. Hanley
*Attorney, Agent, or Firm*—Fisher, Christen & Sabol

[57] ABSTRACT

Process for the continuous production of L-carnitine by the microbiological method. A microorganism of the strain DSM No. 3225 (HK 1331b) type is cultivated in a bioreactor with crotonobetaine and/or γ-butyrobetaine in the presence of a growth substrate. The culture fluid passes outside of the bioreactor in a circulation in which a separation of the cell is carried out. A quantity of cell-free solution, which is as large as the amount fed to the bioreactor as a substrate, is withdrawn from the bioreactor. The L-carnitine is separated from the cell-free solution.

22 Claims, 1 Drawing Figure

FIGURE
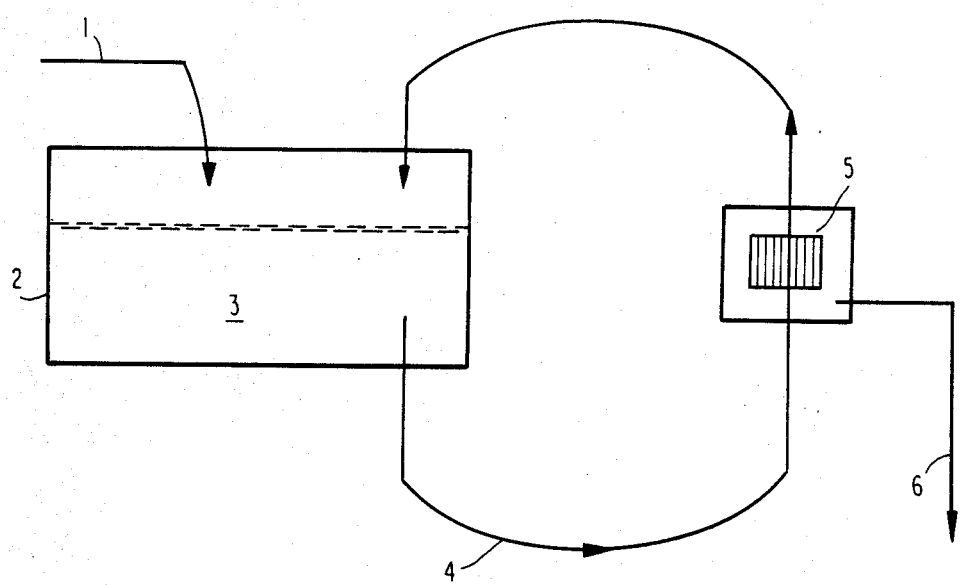

PROCESS FOR THE CONTINUOUS PRODUCTION OF L-CARNITINE

BACKGROUND OF THE INVENTION

1. Field Of The Invention

The invention relates to a continuous process for the production of L-carnitine by the microbiological or biotechnical method.

2. Prior Art Or Related Art

The production of L-carnitine from $\gamma$-butyrobetaine is known. The $\gamma$-butyrobetaine is brought into contact with a hydroxylase-enzyme, liberated from spores of Neurospora crassa (U.S. Pat. No. 4,371,618), in the presence of sodium-2-oxoglutarate, a reducing agent, an iron ion source and a hydroxyl group donor solvent. Such process has the disadvantage of needing a multiplicity of co-factors, which must be externally fed in. Thus, stoichiometric quantities of 2-oxoglutarate are decarboxylized oxidatively in the reaction to succinate. $Fe^{2+}$ is needed as the $O_2$-activator, ascorbate is used in order to keep the iron in the reduced form, and catalase is needed to destroy the harmful $H_2O_2$ which develops in the traces.

Lindstedt et al., "The Formation and Degradation of Carnitine in Pseudomonas", (Biochemistry 6, 1262–1270 (1967)), isolated a microorganism of the species Pseudomonas which grows with $\gamma$-butyrobetaine as a C- and N-source. The first reaction of the composition path was the hydroxylation of the $\gamma$-butyrobetaine to L-carnitine, whereupon the intermediately developing L-carnitine was further completely catabolized into $CO_2$, $H_2O$ and $NH_3$.

If such microorganism was used for the production of L-carnitine, such hydroxylase obtained from bacteria would also have the disadvantageous co-factor-requirements described by Lindstedt et al., "Purification and Properties of $\gamma$-Butyrobetaine Hydroxylase from Pseudomonas sp. AK 1", Biochemistry 16, 2181–2188, (1977).

BROAD DESCRIPTION OF THE INVENTION

An object of the invention is to provide a process which overcomes and/or avoids the above-stated disadvantages of the prior art and mentioned related art. Another object of the invention is to provide a process, which allows in a continuous system or manner, the production of L-carnitine enantio-selectively. A further object of the invention is to provide a process for the production of L-carnitine from crotonobetaine and/or $\gamma$-butyrobetaine by means of the microbiological process. Other objects and advantages are set out herein or are obvious herefrom to one skilled in the art.

The advantages and objects of the invention are achieved by the process of the invention.

As compared to the systems known from the above-description of the prior art, microorganisms used in the invention use $H_2O$, and not $O_2$, as the hydroxyl group donors, as was determined by investigations using $H_2{}^{18}O$ and $^{18}O_2$.

According to the invention, a microorganism of the strain DSM No. 3225 (HK 1331b) type is cultivated in a bioreactor with crotonobetaine and/or $\gamma$-butyrobetaine in the presence of a growth substrate. The culture fluid is guided outside of the bioreactor in a circulation in which a cell separation is carried out, whereby a quantity of cell-free solution, which is as large as the amount fed to the bioreactor as a substrate, is withdrawn from the bioreactor. Finally the L-carnitine is separated from the cell-free solution.

By use of the advantageous invention method of operation, and as a result thereof of the retention of the biomass, a higher productivity as well as a greatly improved longtime stability of the continuous process is achieved.

Preferably crotonobetaine, $\gamma$-butyrobetaine or a mixture thereof is used in a quantity of 0.1 to 10 percent by weight, based on the weight of the culture medium. Preferably dimethylglycine, choline, glutamate, acetate and/or betaine is used as a growth substrate. The growth substrates are preferably used in a quantity of 0.1 to 10 percent by weight, based on the weight of the culture medium. The separation of the cells is accomplished preferably by centrifugation or preferably by ultrafiltration. Preferably a through-flow rate of 0.05 to 0.5 $h^{-1}$ is used.

Preferably $\gamma$-butyrobetaine and/or crotonobetaine, which has been desalted and purified, is used. The $\gamma$-butyrobetaine and/or crotonobetaine prefereably is desalted and purified by electrodialysis or by ion exchange.

The isolation of L-carnitine from the cell-free solution is preferably accomplished by cation exchange chromotography. Or, preferably, the isolation of L-carnitine is accomplished from the cell-free solution by electrodialysis with subsequent recrystallization.

BRIEF DESCRIPTION OF THE DRAWING

In the drawing:

The Figure is a schematic view of a preferred embodiment of the continuous process of the invention.

DETAILED DESCRIPTION OF THE INVENTION

As used herein, all parts, ratios, percentages and proportions are on a weight basis unless otherwise stated herein or otherwise obvious herefrom to one ordinarily skilled in the art.

The preferred microorganism DSM No. 3225 (HK 1331b) is particularly suitable for producing L-carnitine in the continuous process of the invention from crotonobetaine and/or $\gamma$-butyrobetaine and without catabolizing the produced L-carnitine. The new strain DSM 3225 (HK 1331b) was deposited on Feb. 8, 1985, in the German collection of microorganisms (DSM), Gesellschaft fuer Biotechnologische Forschung mbH., Griesebachstrasse 8, 4300 Goettingen, Federal Republic of Germany, under the designation or number DSM 3225. Such deposit of a culture of such new strain of microorganisms in such depository affords permanence of the deposit and ready accessibility thereto by the public if a patent is granted, under conditions which assure (a) that access to the culture will be available during the pendency of the patent application to one determined by the Commissioner to be entitled thereto under 37 C.F.R. 1.14 and 35 U.S.C. 122, and (b) that all restrictions on the availability to the public of the culture so deposited will be irrevocably removed upon the granting of the patent. The applicants or their assigns have provided assurance of permanent availability of the culture to the public through such depository.

Microorganism strain DSM 3225 is obtainable by the following selection methods of the invention:

(a) Microorganisms, which grow with betaine, $\gamma$-butyrobetaine, crotonobetaine and L-carnitine as the C- and N-source, are mutated in the conventional or customary manner.

(b) From the culture obtained by cultivation of the mutated microorganisms, the mutated microorganisms are selected which are stable, do not catabolize L-carnitine and do not grow on L-carnitine, crotonobetaine or γ-butyrobetaine, but do grow with betaine.

(c) From the latter culture, such a strain is selected which is stable, does not catabolize L-carnitine, does not grow on L-carnitine, crotonobetaine or γ-butyrobetaine and shows good growth in a medium which contains L-glutamate as well as γ-butyrobetaine or crotonobetaine.

Preferably, following selection step (b), the microorganisms are selected which excrete L-carnitine and do not grow on L-carnitine, crotonobetaine or γ-butyrobetaine, but do grow with betaine.

Effectively, the mutated microorganisms are cultivated further in a betaine medium and these further-cultivated microorganisms are cultivated even further preferably in an L-carnitine medium in order to carry out selection step (b). The cultivation of strains growing with betaine, γ-butyrobetaine, crotonobetaine and L-carnitine as a C- and N-source is carried out effectively in such a manner that one produces mixed cultures from mixtures of bacteria by inoculation of crotonobetaine nutritional solutions and that, from these cultures, one establishes pure cultures of microorganism decomposing crotonobetaine with the help of traditional microbiological techniques. The mutation of such a culture, which grows with betaine, γ-butyrobetaine, crotonobetaine and L-carnitine as a C- and N-source can be carried out according to known methods. [J. H. Miller, "Experiments in Molecular Genetics", Cold Spring Harbor Laboratory, (1972), pages 121 to 143].

Methods usable effectively for the production of stable mutants are the frame-shift method, the deletion method and the transposon-insertion method. The microorganisms mutated in this way are then subjected to selection step (b), after further cultivation in a betaine medium and transfer into an L-carnitine medium, whereby means of known "counter-selecting agents", [P. Gerhardt et al., (eds.), Manual of methods for General Bacteriology, Am. Soc. for Microbiology, (1981), pages 222 to 242], those microorganisms are selected which are stable, do not catabolize L-carnitine and do not grow on L-carnitine, crotonobetaine or γ-butyrobetaine, but do not grow with betaine.

Starting out from these strains which produce L-carnitine corresponding to step (c), spontaneous well-growing colonies are isolated from the surface of a nutrient medium strengthened with agar, which contains L-glutamate and butyrobetaine (selectively also crotonobetaine or L-carnitine). These strains grow poorly with betaine. Thus, these strains are ideally suited in the continuous process according to the invention with biomass retention, since in a betaine plus butyrobetaine (selectively also crotonobetaine) medium, a productive equilibrium occurs without any additional growth of biomass. The quick growth desirable in the starting phase can be achieved by the addition of L-glutamate.

The preferred strain is the strain DSM No. 3225, (HK 1331b), as well as its descendants and mutants.

The scientific (taxonomic) description of the strain DSM No. 3225 (HK 1331b) is as follows:

| Form (shape) of the cell | rods partly pleomorphic |
|---|---|
| length μm | 1-2 |
| width μm | 0.5-0.8 |
| mobility | + |
| flagellata | peritric |
| gram-reaction | − |
| spores | − |
| formation of poly-β-hydroxybutyrate | − |
| oxidase | + |
| catalase | + |
| growth: | |
| anaerobic | − |
| 37° C. | + |
| 41° C. | − |
| pH 5.6 | − |
| Mac-Conkey-agar | + |
| SS-agar | − |
| cetrimide-agar | − |
| formation of pigment: | |
| not diffusing | − |
| diffusing | − |
| fluorescing | − |
| formation of acid (OF-Test) from: | |
| glucose aerobic | − |
| anaerobic | − |
| fructose aerobic | − |
| ASS glucose | + |
| xylose | + |
| trehalose | + |
| ethanol | − |
| gas formation from glucose | − |
| ONPG | + |
| arginine dihydrolase | − |
| lysine decarboxylase | − |
| phenylalanine deaminase | − |
| ornithine decarboxylase | − |
| $H_2S$ | − |
| Voges-Proskauer | − |
| indol | − |
| nitrite from nitrate | + |
| denitrification | + |
| formation of levan | − |
| lecithinase | − |
| urease | + |
| decomposition of: | |
| starch | − |
| gelatin | − |
| casein | − |
| tyrosin | − |
| Tween 80 | − |
| DNA | + |
| aesculin | + |
| utilization of substrate | |
| acetate | − |
| citrate | − |
| malonate | − |
| glycine | − |
| norleucin | − |
| xylose | + |
| fructose | + |
| glucose | + |
| autotrophic growth with $H_2$ | − |
| 3-ketolactose | − |
| growth: | |
| betaine | + |
| L-carnitine | − |
| γ-butyrobetaine | − |
| crotonobetaine | − |
| L-glutamate and crotonobetaine | + |
| L-glutamate and butyrobetaine | + |
| L-glutamate and L-carnitine | + |

The continuous process of the invention for the production of L-carnitine can be carried out effectively in such a way that a preculture of a microorganism, preferably a microorganism strain DMS 3225, is cultivated in a sterilized, preferably vitamin containing mineral medium [Kulla et al., Arch. Microbiol, 135, 1 (1983), pages 1 to 7], at 20° to 40° C., preferably at 30° C., at an effective pH value of 6 to 8, preferably 7, for 20 to 50 hours, preferably for 30 to 40 hours. This preculture effectively contains 0.1 to 10 percent by weight, preferably 0.1 to 5 percent by weight, of choline, glutamate, acetate, dimethylglycine or betaine as a growth substrate. Particularly preferred is betaine in a quantity of 0.2 to 5 percent by weight.

Furthermore, it is customary with microbiology techniques to add to the preculture also the starting compounds that are to be converted-in this case, γ-butyrobetaine, crotonobetaine or mixtures thereof in a quantity of 0.1 to 10 percent by weight, preferably 0.1 to 5 percent by weight, related to the reaction medium. The γ-butyrobetaine or crotonobetaine can be present as a hydrochloride salt or as a free inner salt as well as in the form of one of its derivatives.

Using the preculture produced according to the process mentioned above, further cultures can be inoculated. These further cultures have effectively the same composition as the precultures.

After that, one can change over to the continuous method of operation of the invention (according to the principle show in FIG. 1).

Effectively one proceeds in such a way that, with a through-flow rate D of 0.05 to $0.5h^{-1}$, preferably 0.07 to $0.12h^{-1}$, one simultaneously pumps γ-butyrobetaine and/or crotonobetaine in a concentration of effectively 1 to 100 g/l, preferably 10 to 50 g/l, and betaine in a concentration of effectively 1 to 100 g/l, preferably 2 to 20 g/l, by medium line 1 into bioreactor 2 (the concentrations are related to 1 l of culture liquid). Culture fluid 3, which is contained in reactor 2, which corresponding to the vitamin-containing mineral medium according to Kulla et al., Arch. Microbiol. 135, 1 (1983), and which contains the L-carnitine-producing strain DSM 3225 (HK 1331b), at the same time is transported outside of bioreactor 2 in circulation line 4, which contains cell separating arrangement 5 (it effectively is equipment for ultrafiltration and centrifugation).

As a result of separation of the cells, one achieves on the one hand, that the active biomass will not be withdrawn from bioreactor 2 but instead is brought back and, on the other hand that the L-carnitine containing cell-free solution 6 can be withdrawn from the circulation. At the same time, one proceeds in such a way that an equally large quantity of cell-free solution 6 is withdrawn from the cell separation as is fed to bioreactor 2 in medium inlet 1. Usually, the concentration of L-carnitine in the cell-free solution 6 is equivalent to the reacted quantity of γ-butyrobetaine or crotonobetaine. Also usually, the cell-free solution 6 contains an additional 5 to 10 percent of unreacted γ-butyrobetaine or crotonobetaine.

The high stability of the system is surprising and unexpected. Thus, for weeks, no loss of activity is observed.

Relief of the culture can be using γ-butyrobetaine and/or the crotonobetaine which previously has been desalinated and purified by means of ion exchanges or by means of electrodialysis.

In order to achieve a 100 percent turnover, one can likewise proceed in such a way that a secondary reaction step is arranged in the form of a cascade.

Obtaining of L-carnitine from cell-free solution 6 can be carried out in such a way that the solution is freed of the charged particles (cations and anions) by means of a laboratory electrodialysis installation. The terminal point of the desalination can be determined conductometrically. At the same time, the salts migrate into the concentrate circulation while the L-carnitine remains as an inner salt (betaine) in the diluent circulation. Thus, yields of L-carnitine in the diluent of more than 95 percent can be achieved after the desalination.

Alternatively to the electrodialysis, it is possible to desalinate the L-carnitine also by means of a strongly acidic cation exchange in the $H^+$-form [see J. P. Vandecasteele, Appl. Environ, Microbiol. 39, 327 (1980), pages 327 to 334]. At the same time, solution is allowed to flow over an ion exchange column for a length of time until the ion exchange is exhausted and L-carnitine breaks through. The anions pass as free acids into the passage. The cations remain on the ion exchange. After neutral washing of ion exchange with water, the L-carnitine can be eluted with aqueous ammonia solution. Thus, yields of L-carnitine of more than 95 percent can be achieved in the ammoniacal eluant.

The diluted L-carnitine solution obtained in the case of electrodialysis as well as by means of ion exchange can be upgraded by a reversing osmosis and can subsequently be azeotropically dehydrated.

The L-carnitine obtained thusly can then be converted into a pure, white L-carnitine by subsequent recrystallization from effectively isobutanol, acetone, methanol, ethanol, or n-butanol. Or, the recrystallization can be conducted using one of such materials in combination with a solvent which dissolves only a small amount of L-carnitine, such as, acetone, ethylacetate, butylacetate, isobutylmethyl ketone and acetonitrile, preferably isobutanol and activated charcoal treatment. According to such process, one can obtain L-carnitine with specific turns of $[\alpha]_D^{25} - 30.5$ to 31.0; c is 1 in $H_2O$ (literature value −30.9°; Strack et al., Hoppe-Seyler's Z.f. physiolog. Chem., 318 (1960), 129) and a content of more than 99 percent (HPLC).

By way of summary, the invention involves the continuous production of L-carnitine from crotonobetaine and/or γ-butyrobetaine using the microbiology way or method.

The pertinent parts of commonly-owned concurrently-filed herewith application Ser. No. 717,698, filed on Mar. 29, 1985, (L.P. 1329), entitled "Process For The Production Of L-Carnitine By Way Of Microbiology", by Hans Kulla and Pavel Lehky are incorporated herein by reference.

The practical use of the invention is illustrated by the following examples:

EXAMPLE 1

A 0.1 l preculture of the strain DSM 3225 (HK 1331b) was cultivated in the following nutrient medium at 30° C. and pH 7.0 for 24 hours:

| Composition of the nutrient medium | |
|---|---|
| L-glutamate | 2 g |
| betaine | 2 g |
| crotonobetaine | 2 g |
| buffer solution | 100 ml |
| Mg—Ca—Fe solution | 25 ml |
| trace elements solution | 1 ml |
| vitamin solution | 1 ml |
| with water on | 1 l |
| Buffer solution | |

-continued

| Composition of the nutrient medium | |
|---|---|
| $Na_2SO_4$ | 1 g |
| $Na_2HPO_4.2H_2O$ | 25.08 g |
| $KH_2PO_4$ | 10 g |
| NaCl | 30 g |
| with water on | 1 l |
| Mg—Ca—Fe solution | |
| $MgCl_2.6H_2O$ | 16 g |
| $CaCl_2.2H_2O$ | 0.58 g |
| $FeCl_3.6H_2O$ | 0.032 g |
| with water on | 1 l |
| Trace elements solution | |
| $ZnSO_4.7H_2O$ | 100 mg |
| $MnCl_2.4H_2O$ | 30 mg |
| $H_3BO_3$ | 300 mg |
| $CoCl_2.6H_2O$ | 200 mg |
| $CuCl_2.2H_2O$ | 10 mg |
| $NiCl_2.6H_2O$ | 22 mg |
| $NaMoO_4.2H_2O$ | 30 mg |
| with water on | 1 l |
| Vitamin solution | |
| pyridoxal.HCl | 10 mg |
| riboflavine | 5 mg |
| nicotinamide | 5 mg |
| thiamine.HCl | 5 mg |
| biotine | 2 mg |
| sodium pantothenate | 5 mg |
| p-aminobenzoic acid | 5 mg |
| folic acid | 2 mg |
| vitamin B 12 | 5 mg |
| with water on | 1 l |

With the preculture, 2 l of nutritional medium of equal composition was inoculated in the fermenter and was cultivated for 24 hours at 30° C. and pH 7. The pH was kept constant at 7.0 by the addition of 8 percent phosphoric acid.

Subsequently, the continuous operation was started. With a flow rate D of 0.09 per hour, the above-described medium containing 15 g/l of betaine and 24.3 g/l of crotonobetaine (desalinated with the help of electrodialysis) without L-glutamate, was pumped through medium inlet 1 into the bioreactor 2. Culture fluid 3, which contained the L-carnitine and the HK 1331b biomass, was continuously pumped in circulation line 4 at the speed of 2 l per min. through a normal ultrafiltration arrangement. The active biomass was brought back into the bioreactor. The clear L-carnitine containing filtrate 6 was pumped off at a flow rate of likewise 0.09 per hour.

According to analysis (HPLC), the filtrate contained 25 g/l of L-carnitine and 2.0 g/l unreacted crotonobetaine. This corresponds to a 92 percent turnover of crotonobetaine and an L-carnitine yield of 99.6 percent, related to the reacted crotonobetaine. The betaine was completely catabolized. After reaching a maximum cell density of about 35 g dry weight per liter, the biomass concentration and the L-carnitine productivity remained constant for at least 1 month.

Isolation of L-carnitine

L-carnitine was isolated from the solution which contained 25 g of L-carnitine, 2 g of crotonobetaine and about 10 g of inorganic salts per liter of solution, as follows:

(1) Desalination

2 Liters of L-carnitine solution was desalinated by means of a commercial strongly acidic cation exchange in the H+-form and subsequently by means of elution with aqueous ammonia. The process was as follows:

400 g of DOWEX® HCR-W2 was placed in an exchange glass column. Then, 2 l of L-carnitine solution was allowed to flow over the ion exchange for about 3 hours. At the same time, the L-carnitine did not yet come through the DOWEX column. After that, the column material was washed out with about 1.5 l of ice water. Subsequently the L-carnitine and crotonobetaine were eluted with 1 l of 5 percent ammonia and 0.5 l of ice water in about 3 hours—1550 ml of ammoniacally desalinated L-carnitine solution was obtained. 30.9 of L-carnitine and 2.47 g of crotonobetaine were found in each liter of the solution. This corresponds to a yield of 96 percent, in the case of desalination by means of ion exchange.

(2) Upgrading

The solution from the desalination using ion exchange (1550 ml) was concentrated at 50° C. and 25 mbar by means of a labor-rotation evaporator. For the removal of the water, the latter was taken out azeotropically with isobutanol on the rotation evaporator under vacuum (50° C., 25 mbar). The residue was dried at 50° C. and 25 mbar (34.05 g). containing 90.7 percent of L-carnitine and 7.2 percent of crotonobetaine. This corresponds to a practically quantitative yield of L-carnitine for the upgrading.

(3) Purification

The purificaton of the crude L-carnitine was accomplished in the same manner as described in Example 2 below. At the same time, a comparable yield and quality was achieved.

EXAMPLE 2

100 ml of the nutritional medium described in Example 1, which contained 2 g/l butyrobetaine instead of the crotonobetaine, was inoculated with strain HK 1331b and was cultivated at 30° C. and pH 7 for 24 hours. In this case, 2 l of the same nutritional medium were inoculated in the bioreactor and were cultivated like the preculture (at 30° C. and pH 7) for 24 hours. After that, the continuous operation was started. The nutrient, which had the following composition:

| desalinated butyrobetaine | 25 g |
|---|---|
| betaine | 0.7 g |
| $MgCl_2.6H_2O$ | 200 mg |
| $CaCl_2.2H_2O$ | 14.5 mg |
| $FeCl_3.6H_2O$ | 0.8 mg |
| $Na_2SO_4$ | 100 mg |
| KCl | 100 mg |
| solution of trace elements | 1 ml |
| vitamin solution | 1 ml |
| with water on | 1 l | was pumped into the bioreactor at a flow rate of 0.09/h. The pH was kept constant at 7 by an addition of 8 percent $H_3PO_4$. As described in Example 1, the culture fluid was continuously filtered and the clear filtrate was collected. After reaching a maximum cell density of about 30 g dry weight per liter, the L-carnitine productivity of the culture remained constant for 4 weeks. 4.5 Liters of filtrate were obtained daily. According to HPLC analysis, the filtrate contained 25 g/l of L-carnitine and 1.9 g/l of butyrobetaine. This corresponds to a 92.4 percent turnover of the educt and to an L-carnitine yield of 97.5 percent, related to the reacted butyrobetaine. The betaine was completely catabolized.

Isolation of L-carnitine

Pure L-carnitine was isolated from the solution which contained about 25 g of L-carnitine, 2 g of butyrobetaine and about 4 g of inorganic salts per liter of solution, as follows:

(1) Desalination

2 Liters of L-carnitine solution was desalinated by means of a customary labor-electrodialysis installation (Berghof BEL-2).

At the same time, the experiment was conducted as follows:

1 Liter of 5 percent sodium sulfate solution was inserted into the electrode circuit, 1.9 l of 0.1 percent cooking salt solution was placed in the concentrate circulation and 2.0 l of l-carnitine was inserted into the diluate circulation. Now, this was electrodialyzed for about 4 hours at a voltage which was limited at 24 volts and a current which was limited at 2 amps. The turn-over velocity of the three circulations was about 1.8 l/min. At the beginning of the dialysis a conductive capacity of about 5 mS/cm was measured in the dialysate circulation (containing the L-carnitine and butyrobetaine). At the end of the electrodialysis, conductivity amounted to about 0.1 mS/cm. The L-carnitine solution in the diluate circulation was pumped off and was washed secondarily with about 200 ml of E-water (ice water). In this diluate L-carnitine solution (2150 ml), 22.1 g of L-carnitine and 1.77 g of butyrobetaine per liter were found analytically, which corresponds to a yield of 95 percent in the case of the desalination by means of electrodialysis. This solution was used for upgrading as explained below.

(2) Upgrading

The solution from the desalination by means of electrodialysis (10 l) was reconcentrated by means of a conventional reversing osmosis-module of 22 g of L-carnitine to about 160 g of L-carnitine/l (1 molar).

At the same time, the experiment was conducted as follows:

The solution to be concentrated was placed in the operating container, and after building up the pressure with nitrogen to about 42 bar, it was turned over by means of a turnover pump for a sufficient length of time until about 8.61 l of permeate had passed through (time needed: 2 to 4 hours). The part retained constituted an approximately 7-times reconcentrated solution, containing 152 g of L-carnitine and 12.1 g of butyrobetaine. Approximately 5 percent of the L-carnitine and of the butyrobetaine passed into the permeate, so that the yield for the upgrading in the case of the reversing osmosis amounted to about 95 percent. Further upgrading of the L-carnitine solution enriched by means of reversing osmosis into crude L-carnitine took place analogously to the method mentioned in Example 1 by evaporation on the rotary evaporator and azeotropic drying with isobutanol, which took place practically quantitatively.

(3) Purification 60 g of crude L-carnitine (approximately 93 percent of L-carnitine and 6 percent of butyrobetaine) and 6 g of activated charcoal were heated in 900 ml of isobutanol to reflux. The activated charcoal was filtered off hot and 580 ml of isobutanol was distilled off the filtrate, whereby the L-carnitine partially crystallized out. 300 ml of acetone was added and the material was cooled to ambient temperature. L-carnitine was subjected to suction and was washed twice with 60 ml of acetone. The recrystallization was carried out for a second time (without treatment with charcoal) in order to completely remove the butyrobetaine. After that, the material was dried at 70° C. and 25 mbar until the weight was constant. Then, 49.5 g of white, not-discolored L-carnitine [HPLC more than 99 percent; specific rotation $[\alpha]_D^{25} - 30.9°$, (c=1, H$_2$O)] was isolated at a yield of 87 percent above both recrystallizations, which corresponds to an average yield of 93 percent per recrystallization. The evaporation residues, 4.76 g from the first recrystallization and 3.46 g from the 2nd recrystallization (mainly L-carnitine and butyrobetaine), could be returned to the fermentation.

What is claimed is:

1. A process for the continuous production of L-carnitine comprising cultivating a microorganism of the strain *Achromobacter xylosoxydans* DSM 3225 (HK 1331b) type in a bioreactor with crotonobetaine and/or γ-butyrobetaine in the presence of a growth substrate, passing the culture fluid outside of the bioreactor in a circulation in which a separation of the cell is carried out, whereby a quantity of cell-free solution, which is as large as the amount fed to the bioreactor as a substrate, is withdrawn from the bioreactor, and separating the L-carnitine from the cell-free solution.

2. The process as claimed in claim 1 wherein crotonobetaine γ-butyrobetaine or a mixture thereof is used in a quantity of 0.1 to 10 percent by weight, in relation to the culture medium.

3. The process as claimed in claim 2 wherein dimethylglycine, choline, glutamate, acetate and/or betaine is used as a growth substrate.

4. The process as claimed in claim 3 wherein the growth substrate is used in a quantity of 0.1 to 10 percent by weight, in relation to the culture medium.

5. The process as claimed in claim 4 wherein the separation of the cells is accomplished by centrifugation.

6. The process as claimed in claim 4 wherein the separation of the cells is accomplished by ultrafiltration.

7. The process as claimed in claim 6 wherein a through-flow rate of 0.05 h$^{-1}$ is used.

8. The process as claimed in claim 7 wherein a γ-butyrobetaine and/or crotonobetaine is used which has been desalted and purified.

9. The process as claimed in claim 8 wherein the γ-butyrobetaine and/or crotonobetaine is desalted and purified by electrodialysis.

10. The process as claimed in claim 8 wherein the γ-butyrobetaine and/or crotonobetaine is desalted and purified by ion exchange.

11. The process as claimed in claim 8 wherein the isolation of L-carnitine from the cell-free solution is accomplished by cation exchange chromotography.

12. The process as claimed in claim 8 wherein the isolation of L-carnitine is accomplished from the cell-free solution by electrodialysis with subsequent recrystallization.

13. The process as claimed in claim 1 wherein dimethylglycine, choline, glutamate, acetate and/or betaine is used as a growth substrate.

14. The process as claimed in claim 1 wherein the growth substrate is used in a quantity of 0.1 to 10 percent by weight, based on the culture medium.

15. The process as claimed in claim 1 wherein the separation of the cells is accomplished by centrifugation.

16. The process as claimed in claim 1 wherein the separation of the cells is accomplished by ultrafiltration.

17. The process as claimed in claim 1 wherein a through-flow rate of 0.05 to 0.5 $h^{-1}$ is used.

18. The process as claimed in claim 1 wherein γ-butyrobetaine and/or crotonobetaine is used which has been desalted and purified.

19. The process as claimed in claim 18 wherein the γ-butyrobetaine and/or crotonobetaine is desalted and purfied by electrodialysis.

20. The process as claimed in claim 18 wherein the γ-butyrobetaine and/or crotonobetaine is desalted and purified by ion exchange.

21. The process as claimed in claim 1 wherein the isolation of L-carnitine from the cell-free solution is accomplished by cation exchange chromotography.

22. The process as claimed in claim 1 wherein the isolation of L-carnitine is accomplished from the cell-free solution by electrodialysis with subsequent recrystallization.

* * * * *